(12) United States Patent
Pavani

(10) Patent No.: US 9,250,194 B1
(45) Date of Patent: Feb. 2, 2016

(54) WIDE FIELD ILLUMINATION FOR WAFER INSPECTION

(71) Applicant: Sri Rama Prasanna Pavani, Palo Alto, CA (US)

(72) Inventor: Sri Rama Prasanna Pavani, Palo Alto, CA (US)

(73) Assignee: Exnodes Inc., Palo Alto, CA (US)

( * ) Notice: Subject to any disclaimer, the term of this patent is extended or adjusted under 35 U.S.C. 154(b) by 0 days.

(21) Appl. No.: 14/511,189

(22) Filed: Oct. 10, 2014

(51) Int. Cl.
| | | |
|---|---|---|
| *G01N 21/00* | (2006.01) | |
| *G01N 21/88* | (2006.01) | |
| *G01N 21/95* | (2006.01) | |

(52) U.S. Cl.
CPC ........ *G01N 21/8806* (2013.01); *G01N 21/9501* (2013.01)

(58) Field of Classification Search
CPC ......... G01N 21/88; G01N 21/00; H04N 7/18; G03B 27/72; G02B 5/0808; B32B 37/04
See application file for complete search history.

(56) References Cited

U.S. PATENT DOCUMENTS

| | | | |
|---|---|---|---|
| 7,068,363 B2 | 6/2006 | Bevis et al. | |
| 7,180,586 B2 | 2/2007 | Neumann et al. | |
| 7,659,973 B2 | 2/2010 | Furman et al. | |
| 8,094,295 B2 | 1/2012 | Hamamatsu et al. | |
| 2005/0146704 A1* | 7/2005 | Gruner ................ | G03F 7/70108 355/71 |
| 2010/0002227 A1* | 1/2010 | Hamamatsu ....... | G01N 21/8806 356/237.2 |
| 2012/0133761 A1* | 5/2012 | Cho, II ..................... | H04N 7/18 348/92 |
| 2014/0254000 A1* | 9/2014 | O'Keefe .................. | F41H 3/00 359/359 |

* cited by examiner

*Primary Examiner* — Tarifur Chowdhury
*Assistant Examiner* — Jamil Ahmed

(57) ABSTRACT

A system and method for illuminating a surface, comprising: providing a reflective layer around said surface; directing an electromagnetic beam to be incident on said layer; aligning said layer, said beam, and said surface so that said beam undergoes a plurality of reflections on said layer for illuminating a predetermined region of said surface, whereby the size of said region is larger than the size of said beam, and the intensity of illumination on said region is higher than the value obtained by multiplying the intensity of said beam and the ratio of the size of said beam to the size of said region.

20 Claims, 19 Drawing Sheets

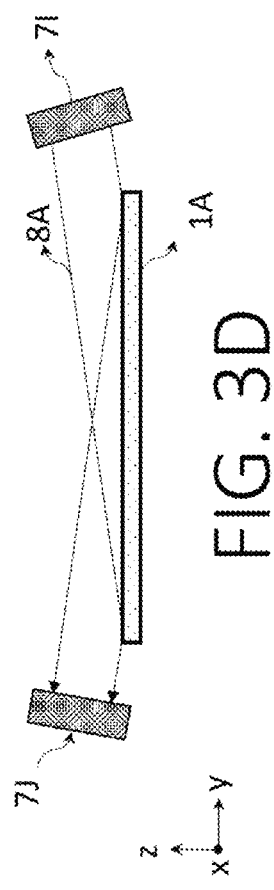
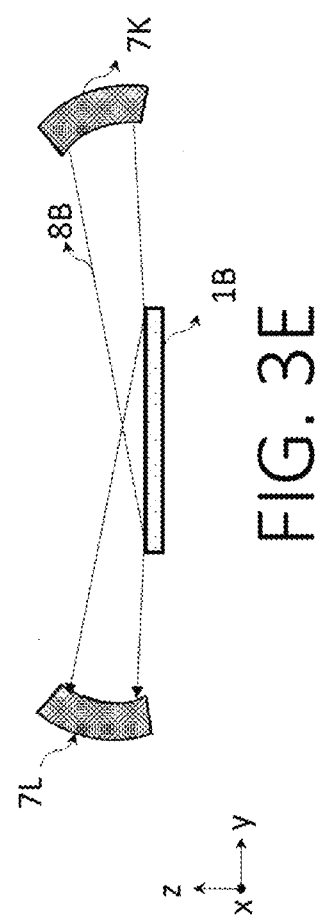

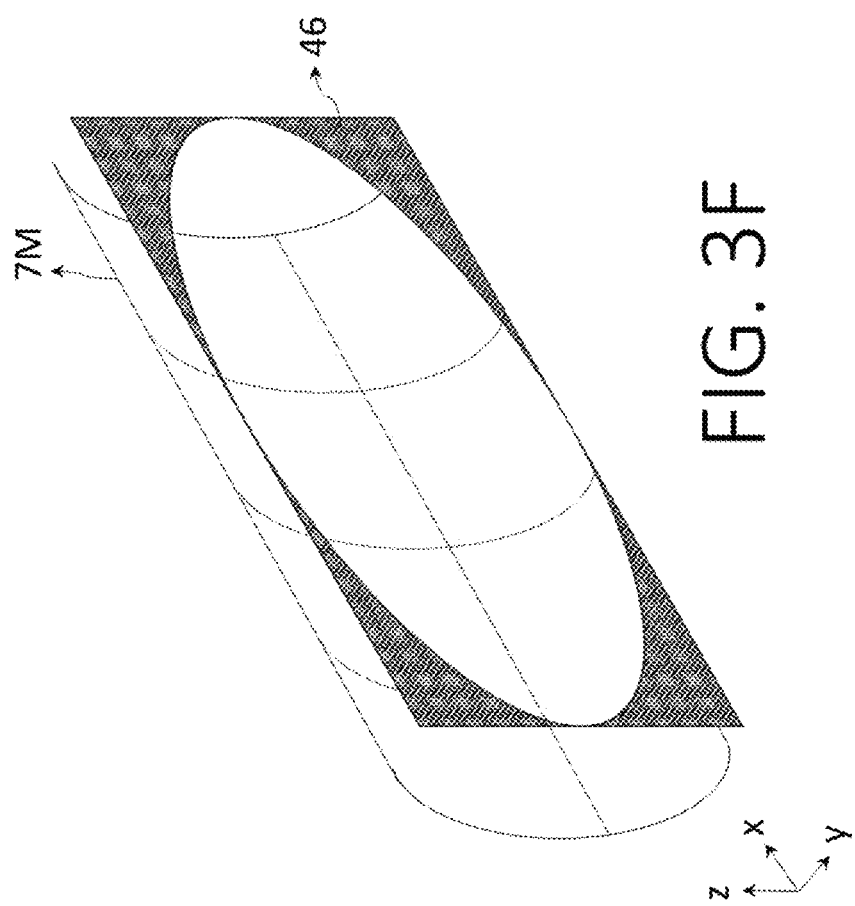

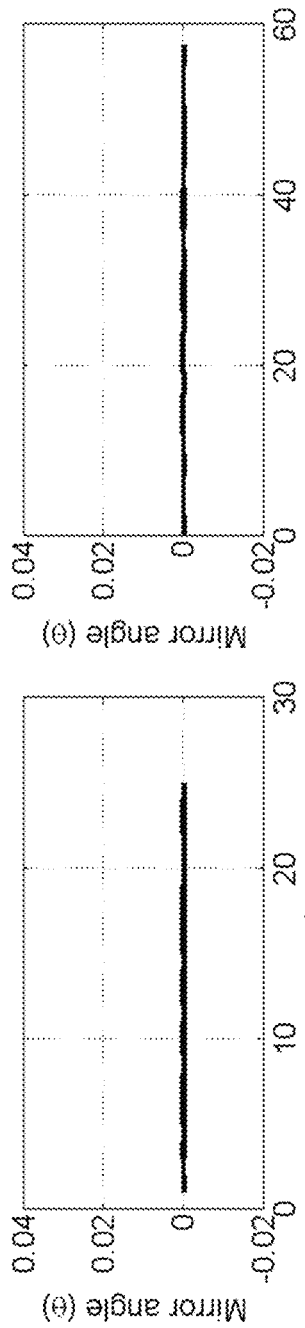
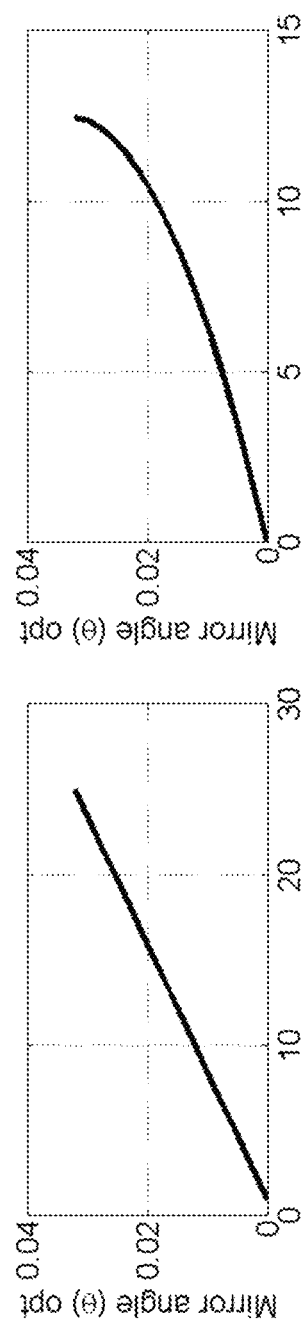
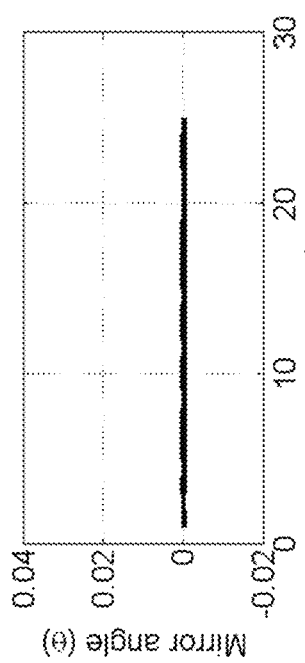
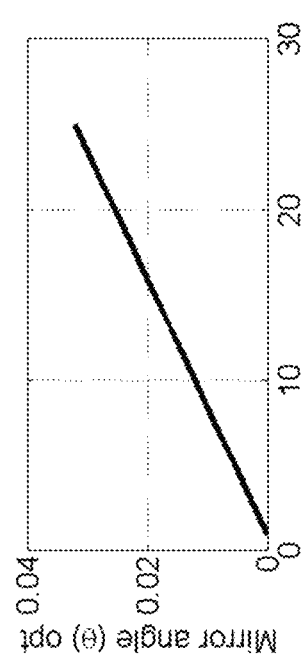
FIG. 3N
FIG. 3P
FIG. 3Q
FIG. 3R

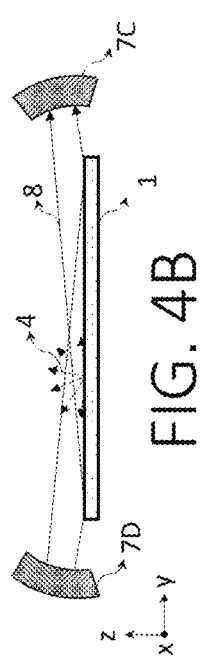
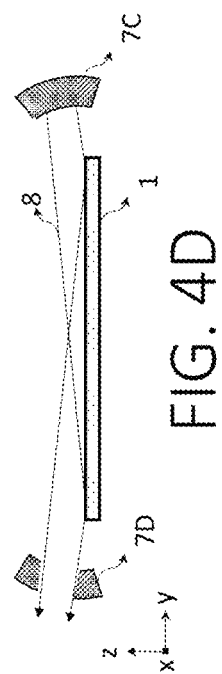
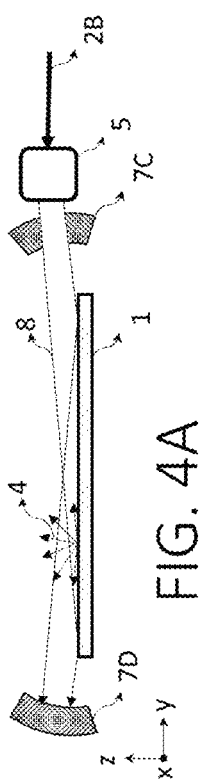
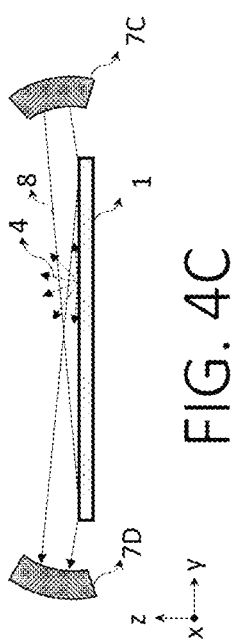

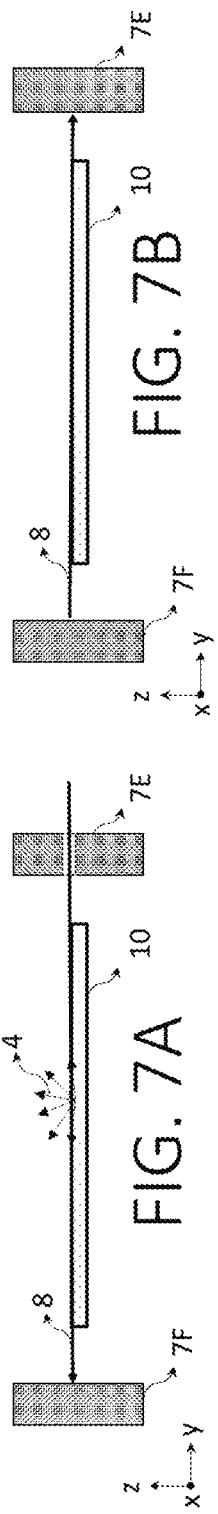
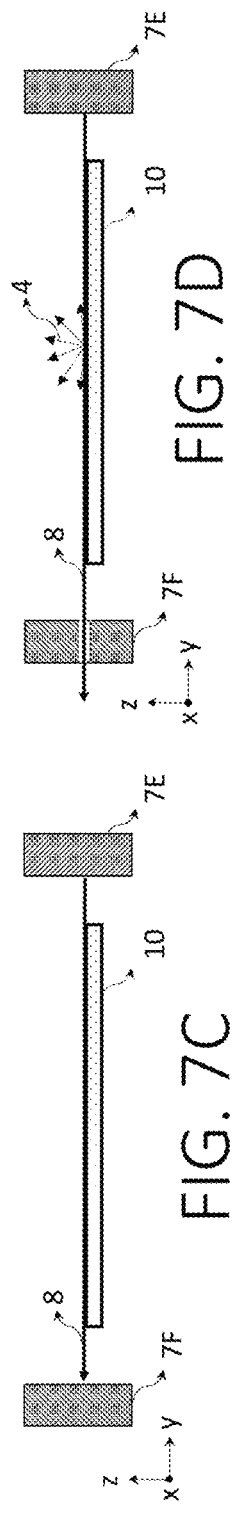

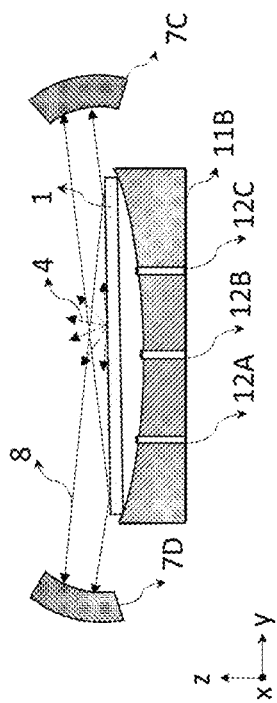
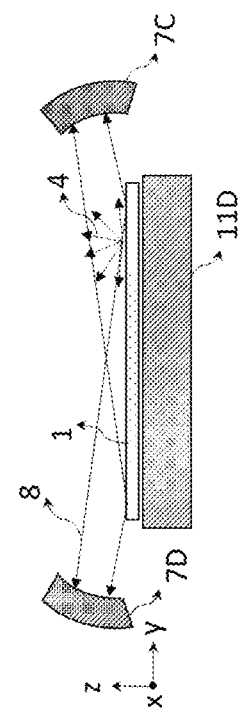
FIG. 8A
FIG. 8B
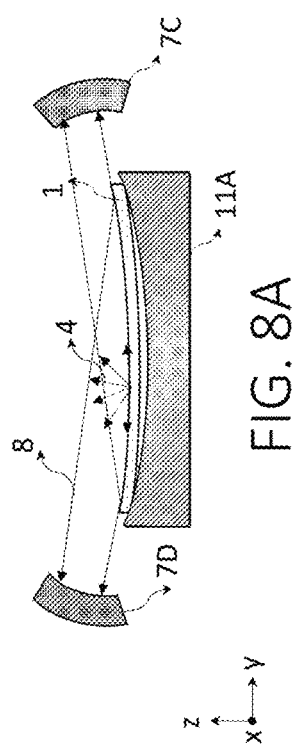
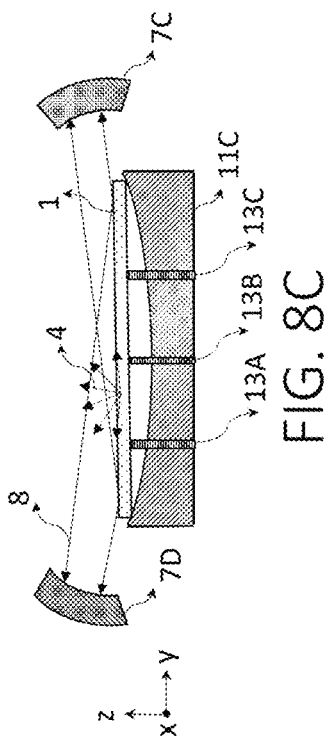
FIG. 8C
FIG. 8D

WIDE FIELD ILLUMINATION FOR WAFER INSPECTION

FIELD OF THE INVENTION

This invention relates generally to optical illumination and more particularly to optical illumination for wafer inspection.

BACKGROUND

Modern electronic devices such as smartphones and high resolution displays are made possible by advances in semiconductor technology. Inside these modern electronic devices lie components known as integrated circuits (IC). ICs provide the processing power and memory that allow the electronic devices to do complex tasks quicker.

ICs are manufactured in semiconductor fabrication facilities (fabs) that employ a variety of semiconductor capital equipment tools maintained in a carefully monitored environment. The capital equipment tools perform hundreds of process steps such as implantation, deposition, photolithography, etching, polishing, and packaging to transform a semiconductor wafer into a number of integrated circuit chips.

The process steps involved in the fabrication of ICs need to be carefully monitored and controlled to maximize production yield. Yield is a percentage value that refers to the ratio of the number of ICs that meet performance specifications in a given batch to the total number of ICs produced in the batch. Maximizing production yield of ICs is important to produce cost-effective electronic devices.

A variety of wafer inspection and metrology tools are employed in semiconductor fabs for monitoring and controlling process steps. Optical tools are used for tasks such as detecting defects on wafers and photolithography masks and for measuring wafer shape, critical dimension, film properties, and overlay.

Detecting yield-limiting defects on wafers, identifying the root cause of such defects, and controlling process parameters to bring defect levels within limits, are important activities in semiconductor fabrication. Advances in semiconductor fabrication technologies have reduced the size of individual components inside ICs from micrometer scale to nanometer scale features. As a result, the size of yield-limiting defects have also come down to the nanometer scale.

Detecting nanometer scale defects with traditional dark field or bright field optical inspection techniques is challenging because nanometer scale defects barely scatter optical radiation. The scattering intensity of defect particles, being proportional to the sixth power of defect diameter, exhibits a strong dependence on defect size. For example, reducing defect size by a factor of 2 results in a reduction in scattering intensity by a factor of 64. In order to detect yield-limiting defects at leading-edge semiconductor technology node, a leading-edge defect inspection tool requires an exponential increase in defect signal detection performance compared to a previous generation tool.

Scattering intensity of defect particles, being inversely proportional to the fourth power of wavelength, exhibits a dependence on wavelength. For example, reducing the wavelength of optical radiation by a factor of 2 increases scattering intensity by a factor of 16. However, developing light sources with high brightness at wavelengths lower than deep ultra violet has been challenging.

Scattering intensity of defect particles also exhibits a linear dependence on the intensity of optical radiation incident on the defects. A factor of 2 increase in the intensity of optical radiation increases scattering intensity also by a factor of 2. However, increasing the intensity of optical radiation increases the risk of damaging the wafer. The risk of laser damage is particularly high in ultraviolet wavelengths where the absorption coefficient of Silicon is high compared to visible and infrared wavelengths. Furthermore, increasing the optical power of a laser increases its complexity, size, and cost.

Accordingly, reducing the wavelength and increasing the intensity of optical radiation are not viable alternatives to adequately compensate the exponential decrease in scattering intensity of decreasing yield-limiting defect sizes. While semiconductor technology node sizes decreased at a fast pace from 130 nm to 14 nm (over 9× reduction) in the last decade, minimum detectable defect sizes decreased at a slower pace from 50 nm to 20 nm (2.5× reduction) in the same time period. This slower pace of improvement in defect detection performance negatively affects the production yield, cost, and timely release of leading-edge semiconductor devices.

Throughput of wafer inspection refers to the number of wafers that can be inspected per hour. Achieving high throughput is desirable in semiconductor fabs to reduce production times and cost.

In traditional wafer inspection tools, there exists a tradeoff between their defect sensitivity and inspection throughput. An increased ability to detect tiny defects comes at the price of reduced throughput. Similarly, an increased inspection throughput comes at the price of reduced sensitivity to tiny defects. This unfortunate tradeoff in traditional wafer inspection tools requires one to choose between two entities that are often equally important to semiconductor fabs.

Dark field wafer inspection tools illuminate a laser spot on the surface of a wafer and collect scattered light originating from the spot. Specular reflection from the spot is carefully prevented from entering the collection optics. Semiconductor wafers are polished to be smooth, so an overwhelming majority of light incident on the spot undergoes specular reflection and is prevented from being collected. The scattered light is so small that it is measured in the units of parts per million. Only a few of the millions of incident photons are eventually collected and detected. The majority of incident optical radiation is wasted. Accordingly, dark field wafer inspection tools suffer from extremely low optical efficiencies.

Darkfield wafer inspection tools inherently suffer from low inspection throughput because of scanning. The diameter of wafers to be inspected can be as large as 450 mm, while the size of the spot illuminated on the wafer is only a few tens of micrometers in size. In order to inspect every point on the wafer, the spot needs to be sequentially scanned to as much as a billion different points of the wafer.

In traditional dark field wafer inspection, techniques to improve inspection throughput by increasing the spot size of inspection results in a decrease in defect sensitivity because of two reasons. Firstly, the increase in spot size leads to a reduction in intensity of incident optical radiation on a defect, leading to a proportional reduction in the intensity of scattered light from the defect. Secondly, increasing the spot size leads to an increase in a background nuisance signal called haze. Haze refers to scattered radiation from surface roughness in wafer. Although the magnitude of surface roughness in a wafer is smaller than yield-limiting defect sizes, the somewhat uniform presence of surface roughness throughout the spot area (as opposed to isolated defects) could create a net haze signal large enough to overwhelm the signal from defects. This in turn leads to reduced defect sensitivity.

In traditional dark field wafer inspection, techniques to improve inspection throughput by increasing the speed of scanning also results in a decrease in defect sensitivity. The higher the scanning speed, the smaller the amount of time the spot spends at each point on the wafer. The amount of scattered radiation collected and detected from a point on the wafer reduces as the amount of time the spot spends at the point is reduced. Therefore, increasing scanning speed leads to a reduction in defect signal, leading to a reduction in defect sensitivity.

Traditional dark-field illumination systems used for wafer inspection suffer from a number of disadvantages. a) reduced defect sensitivity; b) reduced inspection throughput; c) trade-off between defect sensitivity and inspection throughput; d) extremely low optical efficiency; e) large and complex laser sources and illumination systems; f) complex scanning systems; g) change in wafer properties such as shape due to high speed scanning; h) reduced reliability because of motion of components during imaging; and i) increased cost.

Accordingly, there is a need for an improved illumination system in wafer inspection systems that can improve defect sensitivity; improve inspection throughput; break the trade-off between defect sensitivity and inspection throughput; offer high optical efficiencies; reduce complexity of laser sources and illumination systems; reduce complexity of scanning systems; preserve wafer properties such as wafer shape during inspection; increase reliability; and reduce cost of the illumination system.

SUMMARY

The invention is a system and method for illuminating a wide region of a surface with high intensity using a plurality of reflections.

In some embodiments, the invention is a system for illuminating a wide region of a surface with high intensity. The system comprising: a reflective layer around said surface; an electromagnetic beam incident on said layer; means for aligning said layer, said beam, and said surface so that said beam undergoes a plurality of reflections on said layer for illuminating a predetermined region of said surface, whereby the size of said region is larger than the size of said beam, and the intensity of illumination on said region is higher than the value obtained by multiplying the intensity of said beam and the ratio of the size of said beam to the size of said region.

In some embodiments, the invention is a method for illuminating a wide region of a surface with high intensity. The method comprising: providing a reflective layer around said surface; directing an electromagnetic beam to be incident on said layer; aligning said layer, said beam, and said surface so that said beam undergoes a plurality of reflections on said layer for illuminating a predetermined region of said surface, whereby the size of said region is larger than the size of said beam, and the intensity of illumination on said region is higher than the value obtained by multiplying the intensity of said beam and the ratio of the size of said beam to the size of said region.

BRIEF DESCRIPTION OF THE DRAWINGS

FIG. 3D illustrates a cross-section of reflective layers, located within Rayleigh range of beam, producing a large spot size on surface, in accordance with the invention.

FIG. 3E illustrates a cross-section of reflective layers, located outside Rayleigh range of beam, producing a small spot size on surface, in accordance with the invention.

FIG. 3F shows a mask designed to attenuate reflection from predetermined regions of a reflective layer, in accordance with the invention.

FIG. 3N shows a plot of the curvature of a reflective layer with respect to spot count, in accordance with the invention.

FIG. 3P shows a plot of the curvature of a reflective layer with respect to spot position, in accordance with the invention.

FIG. 3Q shows a plot of the optimized curvature of a reflective layer with respect to spot count, in accordance with the invention.

FIG. 3R shows a plot of the optimized curvature of a reflective layer with respect to spot position, in accordance with the invention.

FIG. 4A illustrates a cross-section showing the entry of a beam through a reflective layer located on the right, followed by reflection on a wafer surface, and incidence on another reflective layer located on the left, in accordance with the invention.

FIG. 4B illustrates a cross-section showing the reflection of a beam at a reflective layer located on the left, followed by reflection on a wafer surface, and incidence on another reflective layer located on the right, in accordance with the invention.

FIG. 4C illustrates a cross-section showing the reflection of a beam at a reflective layer located on the right, followed by reflection on a wafer surface, and incidence on another reflective layer located on the left, in accordance with the invention.

FIG. 4D illustrates a cross-section showing the reflection of a beam at a reflective layer located on the right, followed by reflection on a wafer surface, and exit through another reflective layer located on the left, in accordance with the invention.

FIG. 7A illustrates a cross-section showing the entry of a beam through a flat reflective layer located on the right, followed by illumination of a surface at grazing angle, and incidence on another flat reflective layer located on the left, in accordance with the invention.

FIG. 7B illustrates a cross-section showing the reflection of a beam at a flat reflective layer located on the left, followed by illumination of a surface at grazing angle, and incidence on another flat reflective layer located on the right, in accordance with the invention.

FIG. 7C illustrates a cross-section showing the reflection of a beam at a flat reflective layer located on the right, followed by illumination of a surface at grazing angle, and incidence on another flat reflective layer located on the left, in accordance with the invention.

FIG. 7D illustrates a cross-section showing the reflection of a beam at a flat reflective layer located on the right, followed by illumination of a surface at grazing angle, and exit through another flat reflective layer located on the left, in accordance with the invention.

FIG. 8A depicts a cross-section showing the illumination of a curved surface, in accordance with the invention.

FIG. 8B depicts a cross-section showing the use of a gas vent for holding a surface flat, in accordance with the invention.

FIG. 8C depicts a cross-section showing the use of a supporting structure that makes contact with the surface to hold the surface flat, in accordance with the invention.

FIG. 8D depicts a cross-section showing the illumination of a flat surface, in accordance with the invention.

DETAILED DESCRIPTION OF THE PREFERRED EMBODIMENTS

Figure 1:
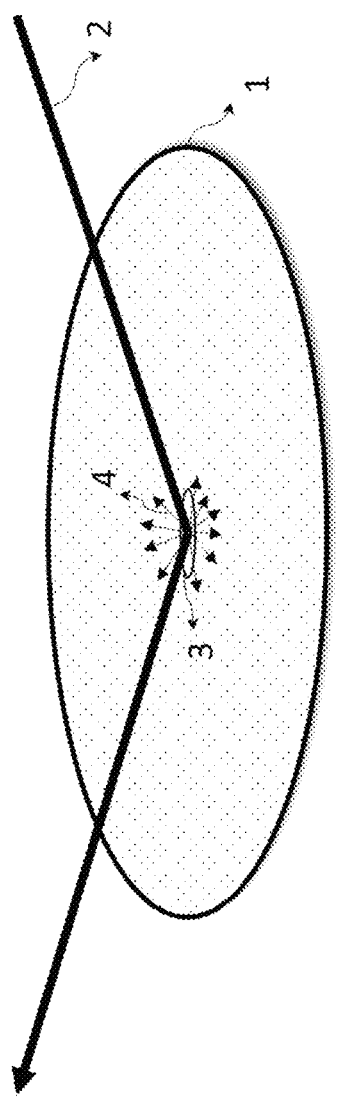
FIG. 1 shows a traditional dark-field surface illumination, according to prior art.

The invention provides an improvement over a traditional dark-field illumination system shown in FIG. 1. In the traditional system of FIG. 1, a surface 1 is illuminated with a beam 2 to create a spot 3 on the surface. The area of the spot is much smaller than the area of the surface. Majority of the light incident on the surface undergoes specular reflection and is wasted. An extremely small fraction of light (few photons per million incident photons) is scattered from the spot if the region of the surface at the location of the spot has a defect. This small scattered light 4 may be used for detecting the defect. The scattered light 4 may also have contributions from surface roughness of the surface at the location of the spot.

The system of FIG. 1 has numerous drawbacks: a) reduced defect sensitivity due to wastage of light that undergoes specular reflection; b) reduced inspection throughput because of the requirement to scan a small spot throughout the area of a large surface; c) trade-off between defect sensitivity and inspection throughput due to sequential scanning of the surface; d) extremely low optical efficiency due to the wastage of light that undergoes specular reflection; e) large and complex laser sources and illumination systems that are necessitated by low optical efficiency; f) complex scanning systems required to scan the spot relative to the surface with high precision and high speed; g) change in wafer properties such as shape due to air currents caused by high speed scanning; h) reduced reliability because of high speed motion of components during imaging; and i) increased cost to support a complex yet inefficient architecture.

Figure 2:
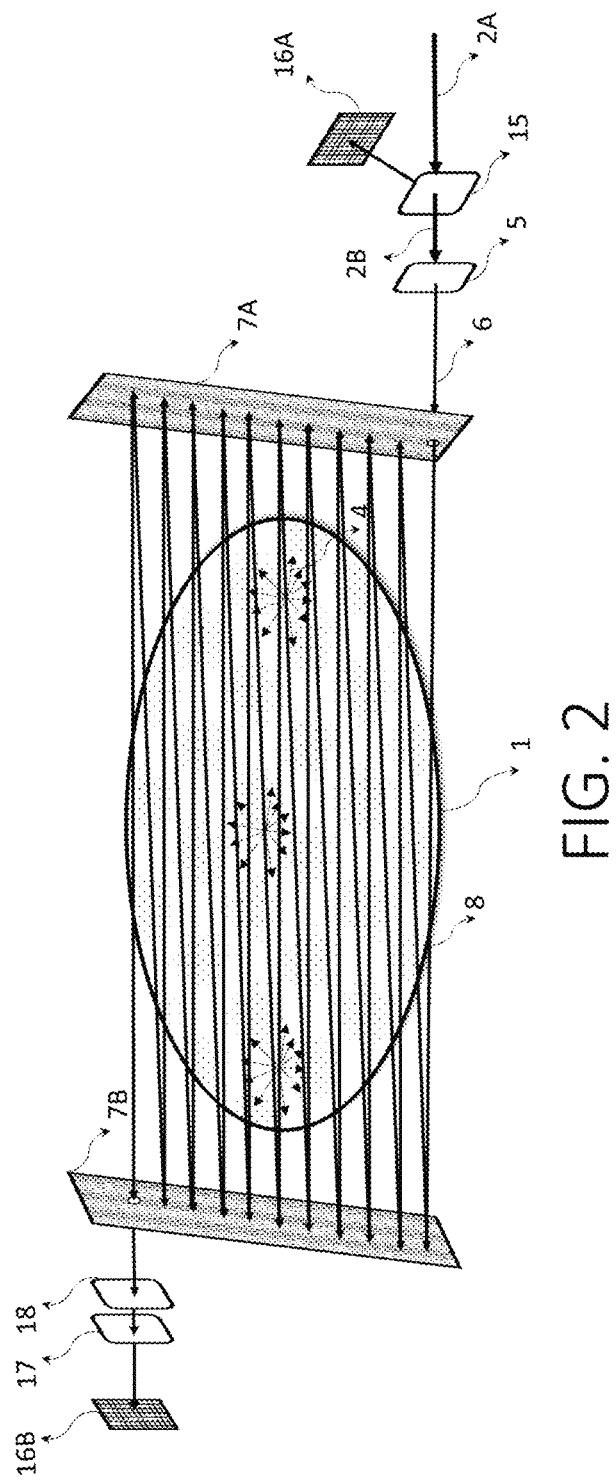
FIG. 2 illustrates a wide field surface illumination having a high intensity, in accordance with the invention.

FIG. 2 shows an improved illumination system, according to some embodiments of the invention. An electromagnetic beam 2A is incident on a beam splitter 15 to reflect a small portion of light on to an image sensor 16A. The image sensor 16A detects the position of the beam. A substantial majority of the beam is transmitted through beam splitter 15. The transmitted beam 2B is incident on a beam expander 5. The beam expander 5 is an optical element that modifies the shape of the beam 2B in order to create a line illumination on surface 1. A variety of surface shapes, including cylinder and cuboid, may be used in accordance with the invention. In some embodiments, surface 1 may be a wafer made of materials including silicon, silicon on insulator, film coatings, germanium, compound semiconductors, and glass. The beam expander may be implemented as a diffractive optical element or a refractive optical element to generate a spot with aspect ratio larger than unity. The aspect ratio of a beam, computed from a spot produced by the beam, is the ratio of the larger dimension to the smaller orthogonal dimension of the spot. The expanded beam 6 propagates through a reflective layer 7A located to the right of the surface 1. The expanded beam 8 is reflected on a second reflective layer 7B located to the left of the surface 1. The beam 8 undergoes a plurality of reflections on reflective layer 7A and reflective layer 7B to illuminate a predetermined region of surface 1. In some embodiments, the predetermined region could include the entire area of surface 1. The size of the predetermined region on surface 1 is larger than the size of said beam 8, and the intensity of illumination on the region is higher than the value obtained by multiplying the intensity of beam 8 and the ratio of the size of beam 8 to the size of the region. Defects present on surface 1 generate scattered light 4. Roughness of surface 1 may also generate scattered light 4. Upon illumination of surface 1, the expanded beam 8 propagates through reflective layer 7B and passes through a focusing optical element 18 and a neutral density filter 17. A second image sensor 16B detects the beam. Images are captured from image sensor 16B, and processed to find beam position by computing the peak, centroid, or a similar parameter indicating spot position.

In some embodiments, the reflective layers 7A and 7B are designed to focus the expanded beam 8 on surface 1, and to have the beam 8 illuminate the predetermined region of interest on surface 1. The position of beam 8 measured from image sensor 16B correlates with the angle of incidence of beam 8 and illumination intensity profile on surface 1. This position data may be used to align the reflective layer 7A, reflective layer 7B, surface 1, and beam 2A to achieve a uniform illumination intensity profile on surface 1. Aligning a component may involve changing the three dimensional position and three dimensional orientation of the component.

The illumination system in FIG. 2 presents numerous improvements over a traditional dark-field illumination system. The improvements include: a) improved optical efficiency due to reduced wastage of beam energy, achieved by reusing a beam for illuminating numerous points on surface; b) improved throughput enabled by a beam illuminating a wide region of interest on surface; c) simpler laser sources and illumination systems allowed by improved optical efficiency; d) elimination of need for high precision and high speed scanning systems, leading to simpler mechanical architecture; e) improved sensitivity achieved as a result of high intensity of illumination and lack of surface motion; f) decoupling of defect sensitivity from throughput enabled by wide area illumination; e) no change in surface properties such as shape allowed by the elimination of necessity move a surface relative to spot in order to achieve wide area illumination; f)

increased reliability because of lack of high speed motion of components; and g) decreased cost as a result of simpler and efficient architecture.

Figure 3A:
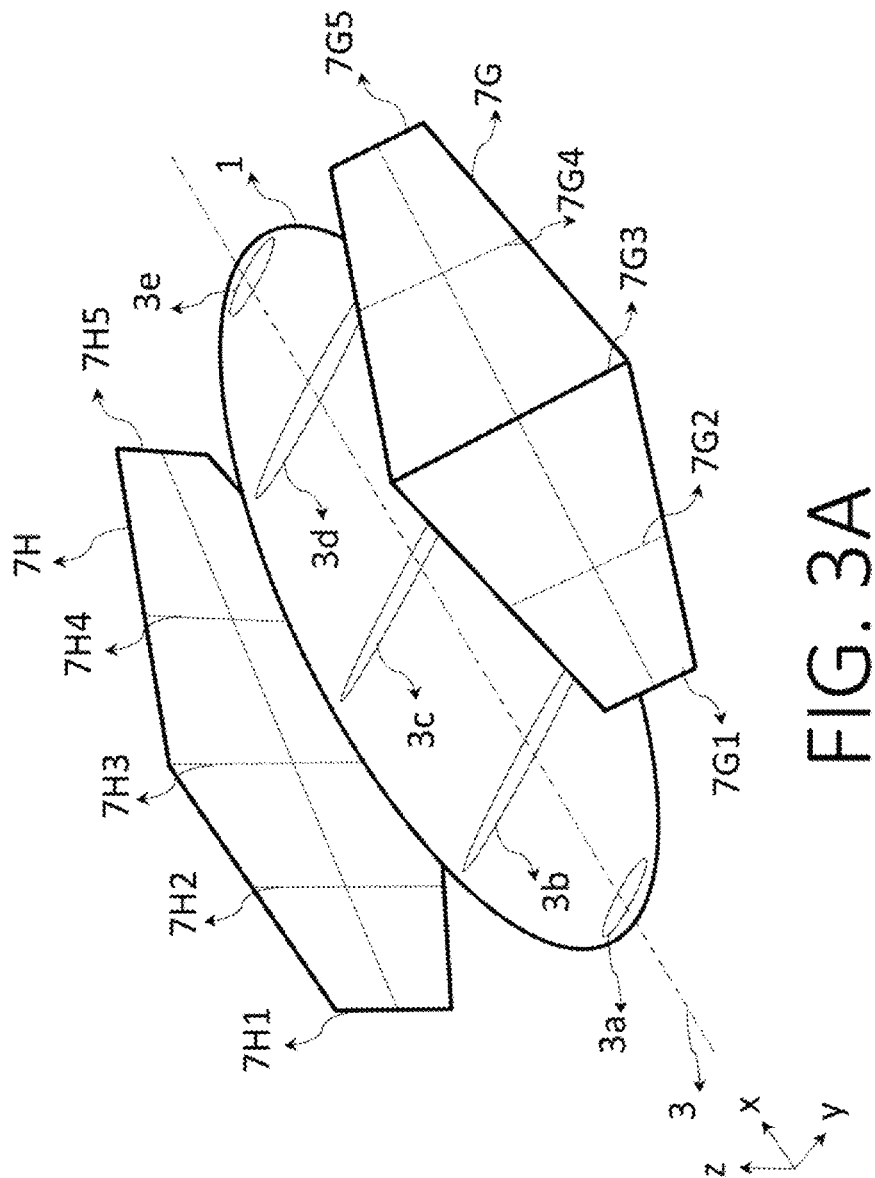
FIG. 3A depicts flat reflective layers, located within Rayleigh range of beam, producing different spot sizes on surface, in accordance with the invention.

FIG. 3A depicts two flat reflective layers, 7G and 7H, designed to produce different spot sizes on a cylindrical surface 1, according to some embodiments of the invention. The reflective layers are flat mirrors with their reflective surfaces facing towards surface 1. The reflective layers, 7G and 7H, are designed to illuminate elongated spots centered on line 3, which is a line along x-axis passing through the center of surface 1. The reflective layers, 7G and 7H, are located within the Rayleigh range of a beam used to illuminate surface 1. Rayleigh range is the optical distance, measured along the propagation axis of a beam, within which the width of the beam is less than $\sqrt{2}w_0$, where $w_0$ is the width of the beam at its waist (focal plane). The aperture of reflective layers, 7G and 7H, are designed to illuminate different spot sizes according to the shape of surface 1. Aperture of a reflective layer refers to the size of the reflective layer along z axis. Aperture sizes at 7G3 and 7H3 are large to generate a large spot size 3c to match the large central chord length (equal to diameter at center) of surface 1. On the other hand, aperture sizes at 7G1, 7H1, 7G5, 7H5 are small to generate a small spot size, 3a and 3e, to match the small upper and lower chord lengths of surface 1. Similarly, aperture sizes at 7G2, 7H2, 7G4, and 7H4 are intermediate to generate intermediate spot sizes, 3b and 3d, to match intermediate chord lengths on surface 1. The curvature about x axis at 7G1, 7G2, 7G3, 7G4, and 7G5 are substantially flat (zero curvature) since the divergence of a beam is minimal within its Rayleigh range. Similarly, the curvature about x axis at 7H1, 7H2, 7H3, 7H4, and 7H5 are also substantially flat. Curvature about z-axis of reflective layers, 7G and 7H, may be substantially flat to achieve a uniform spot density on surface 1. However, curvature about z-axis of reflective layers, 7G and 7H, may be made concave or convex to achieve non-uniform spot density on surface 1. Such non-uniform spot density may be desirable to compensate for effects such as losses in reflection or losses due to non-uniform aperture of reflective layers. In some embodiments, reflective layers, 7G and 7H, may have a uniform aperture size for all x positions to generate a uniform spot size throughout surface 1. Such a uniform spot size may be desirable for illuminating rectangular or square surface regions.

Figure 3B:
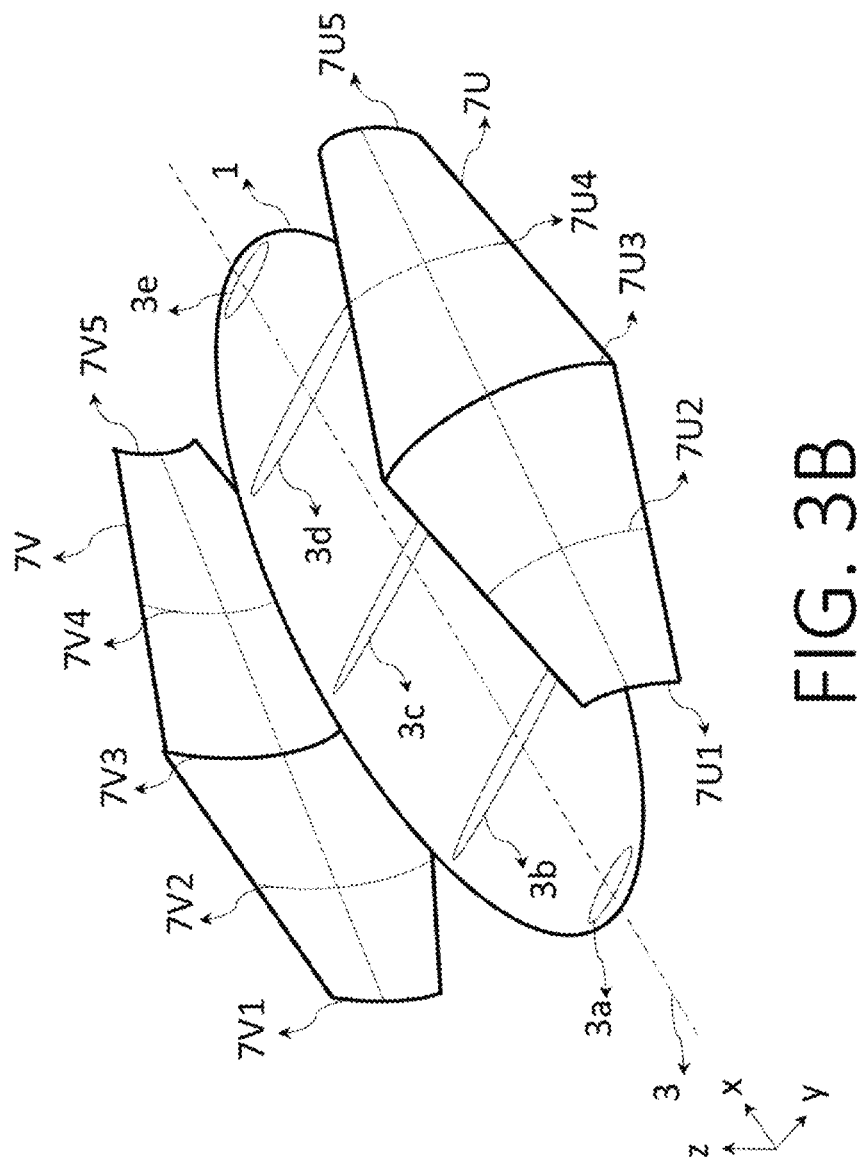
FIG. 3B depicts curved reflective layers, located within Rayleigh range of beam, producing different spot sizes on surface, in accordance with the invention.

FIG. 3B depicts two curved reflective layers, 7U and 7V, designed to produce different spot sizes on a cylindrical surface 1, according to some embodiments of the invention. The reflective layers are curved mirrors with their reflective surfaces facing towards the surface 1. The reflective layers, 7U and 7V, are designed to illuminate elongated spots centered on line 3. The reflective layers, 7U and 7V, are located within the Rayleigh range of a beam used to illuminate surface 1. The aperture of reflective layers, 7U and 7V, are designed to illuminate different spot sizes according to the shape of surface 1. Aperture sizes at 7U3 and 7V3 are large to generate a large spot size 3c to match the large central chord length of surface 1. On the other hand, aperture sizes at 7U1, 7V1, 7U5, 7V5 are small to generate a small spot size, 3a and 3e, to match the small upper and lower chord lengths of surface 1. Similarly, aperture sizes at 7U2, 7V2, 7U4, and 7V4 are intermediate to generate intermediate spot sizes, 3b and 3d, to match intermediate chord lengths on surface 1. The curvature about x axis at 7U1, 7U2, 7U3, 7U4, and 7U5 are curved to generate focused spots that are produced by the waist region of beam. Curvature about x axis compensates for the minimal divergence of beam incurred due to propagation from reflective layers, 7U and 7V, to line 3. The divergence is only minimal because the reflective layers are within the Rayleigh range of the beam. Similarly, the curvature about x axis at 7V1, 7V2, 7V3, 7V4, and 7V5 are curved to generate focused spots that are produced by the waist region of beam. In some embodiments, curvature about x axis results in a reflection layer that is a concave cylindrical mirror with the reflective region facing towards surface 1. Curvature about z-axis of reflective layers, 7U and 7V, may be substantially flat to achieve a uniform spot density on surface 1. However, curvature about z-axis of reflective layers, 7U and 7V, may be made concave or convex to achieve non-uniform spot density on surface 1. Such non-uniform spot density may be desirable to compensate for effects such as losses in reflection or losses due to non-uniform aperture of reflective layers. In some embodiments, reflective layers, 7U and 7V, may have a uniform aperture size for all x positions to generate a uniform spot size throughout surface 1. Such a uniform spot size may be desirable for illuminating rectangular or square surface regions.

Figure 3C:
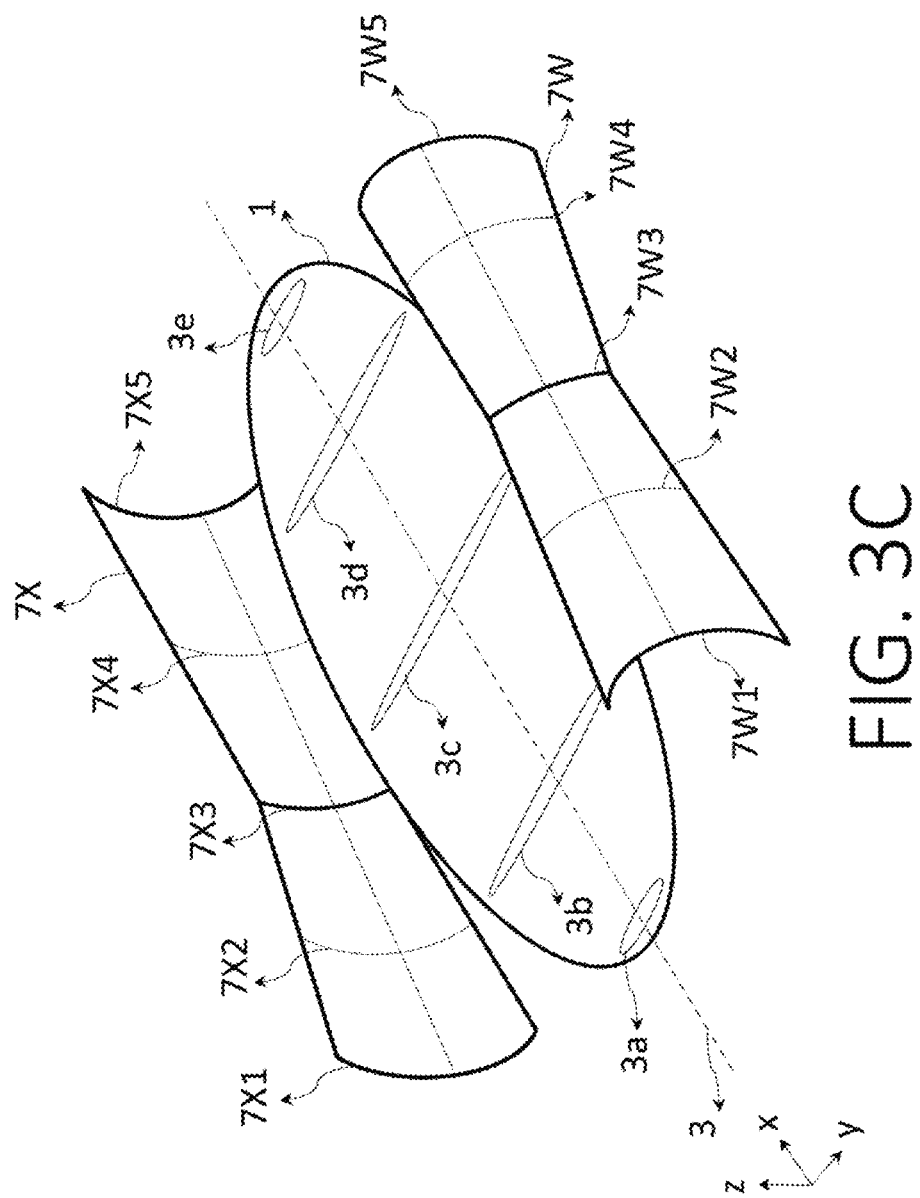
FIG. 3C depicts reflective layers, located outside Rayleigh range of beam, producing different spot sizes, in accordance with the invention.

FIG. 3C depicts two curved reflective layers, 7W and 7X, designed to produce different spot sizes on a cylindrical surface 1, according to some embodiments of the invention. The reflective layers are curved mirrors with their reflective surfaces facing towards the surface 1. The reflective layers, 7W and 7X, are designed to illuminate elongated spots (line) centered on line 3. The reflective layers, 7W and 7X, are located outside the Rayleigh range of a beam used to illuminate surface 1. The aperture of reflective layers, 7W and 7X, are designed to illuminate different spot sizes according to the shape of surface 1. Aperture sizes at 7W3 and 7X3 are small to generate a large spot size 3c to match the large central chord length of surface 1. On the other hand, aperture sizes at 7W1, 7X1, 7W5, 7X5 are large to generate a small spot size, 3a and 3e, to match the small upper and lower chord lengths of surface 1. Similarly, aperture sizes at 7W2, 7X2, 7W4, and 7X4 are intermediate to generate intermediate spot sizes, 3b and 3d, to match intermediate chord lengths on surface 1. The curvature about x axis at 7W1, 7W2, 7W3, 7W4, and 7W5 are curved to generate focused spots that are produced by the waist region of beam. Curvature about x axis compensates for the substantial divergence of beam incurred due to propagation from reflective layers, 7W and 7X, to line 3. The divergence is substantial because the reflective layers are outside the Rayleigh range of the beam. Similarly, the curvature about x axis at 7X1, 7X2, 7X3, 7X4, and 7X5 are curved to generate focused spots that are produced by the waist region of beam. In some embodiments, curvature about x axis results in a reflection layer that is a concave cylindrical mirror with the reflective region facing towards surface 1. Curvature about z-axis of reflective layers, 7W and 7X, may be substantially flat to achieve a uniform spot density on surface 1. However, curvature about z-axis of reflective layers, 7W and 7X, may be made concave or convex to achieve non-uniform spot density on surface 1. Such non-uniform spot density may be desirable to compensate for effects such as losses in reflection or losses due to non-uniform aperture of reflective layers. In some embodiments, reflective layers, 7W and 7X, may have a uniform aperture size for all x positions to generate a uniform spot size throughout surface 1. Such a uniform spot size may be desirable for illuminating rectangular or square surface regions.

FIG. 3D illustrates a cross-section of reflective layers, 7I and 7J, located within Rayleigh range of beam, according to some embodiments of the invention. The aperture of reflective layers, 7I and 7J, are designed to produce a large spot size on surface 1A. When the reflective layers are located within the Rayleigh range, the size of their aperture positively correlates with spot size. That is, an increase in aperture size increases spot size, and a decrease in aperture size decreases spot size. This is because beam 8A is substantially collimated and substantially divergence free within Rayleigh range. In some embodiments, the curvature of reflective layers, 7I and 7J, about x axis is substantially flat since the divergence of a beam is minimal within its Rayleigh range. In some embodiments, the curvature of reflective layers, 7I and 7J, about x axis is minimally curved to generate focused spots on surface 1A that are produced by the waist region of beam. Curvature about x axis compensates for the minimal divergence of beam incurred due to propagation from reflective layers, 7I and 7J, to surface 1A.

FIG. 3E illustrates a cross-section of reflective layers, 7K and 7L, located outside Rayleigh range of beam, according to some embodiments of the invention. The aperture of reflective layers, 7K and 7L, are designed to produce a small spot size on surface 1B. When the reflective layers are located outside the Rayleigh range, the size of their aperture negatively correlates with spot size. That is, an increase in aperture size decreases spot size, and a decrease in aperture size increases spot size. This is because beam 8B exhibits a substantial divergence outside Rayleigh range. In some embodiments, the curvature of reflective layers, 7K and 7L, about x axis is curved to generate focused spots on surface 1A that are produced by the waist region of beam. Curvature about x axis compensates for the substantial divergence of beam incurred due to propagation from reflective layers, 7K and 7L, to surface 1B.

FIG. 3F shows a mask 46 designed to attenuate reflection from predetermined regions of a reflective layer 7M, according to some embodiments of the invention. The shape of mask 46 is designed to generate desired spot sizes on a surface. The factor affecting the shape of mask include: a) shape of surface, b) Rayleigh range of beam, c) position and orientation of mask 46 and reflective layer 7M relative to surface. In some embodiments, spot sizes on surface positively correlate with the shape of surface. Rayleigh range of beam determines the relationship between the aperture size of mask and spot size. Aperture size of mask 7M refers to size of mask measured along z dimension at a particular x coordinate. When reflective layer 7M is within Rayleigh range of beam, the aperture size positively correlates with spot size. And when reflective layer 7M is outside Rayleigh range of beam, the aperture size negatively correlates with spot size. In some embodiments, mask 46 may absorb portions of the beam to attenuate reflection from predetermined regions of a reflective layer 7M. In some embodiments, mask 46 and reflective layer 7M may have uniform aperture for all x positions to generate a uniform spot size throughout surface 1. Such a uniform spot size may be desirable for illuminating rectangular or square surfaces.

Figure 3G:
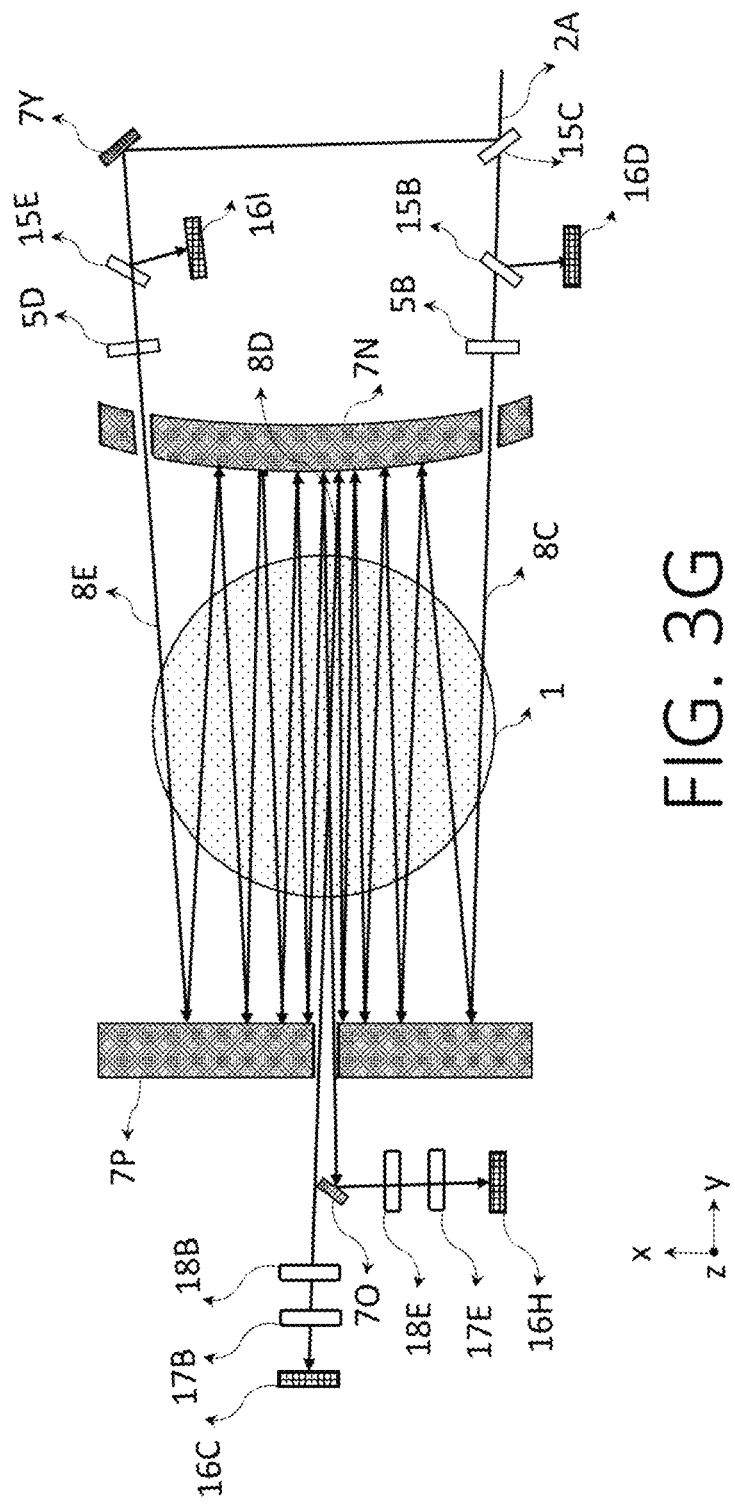
FIG. 3G illustrates reflective layers designed to increase number of reflections in central region of a surface, in accordance with the invention.

FIG. 3G illustrates reflective layers, 7N and 7P, designed to increase number of reflections in central region of a surface 1, according to some embodiments of the invention. An electromagnetic beam 2A is incident on a beam splitter 15C to generate transmitted and reflected beams. The transmitted beam from beam splitter 15C is incident on another beam splitter 15B. The reflected beam from beam splitter 15C is incident on a mirror 7Y and is incident on another beam splitter 15E. The beam splitters 15B and 15E generate transmitted and reflected beams. While the reflected beam from beam splitter 15B is detected by image sensor 16D, the reflected beam from beam splitter 15E is detected by image sensor 16I. The transmitted beam from beam splitter 15B is incident on beam expander 5B to generate expanded beam 8C, and the transmitted beam from beam splitter 15E is incident on beam expander 5D to generate expanded beam 8E. The expanded beams, 8C and 8E, are incident on reflective layer 7P. The expanded beams, 8C and 8E, undergo a plurality of reflections between reflective layers, 7P and 7N, to illuminate surface 1. In some embodiments, beam 8C illuminates a region of surface 1 that is different from the region of surface 1 illuminated by beam 8E. The reflective layers, 7P and 7N, are designed to generate an increased spot density in the central region of surface 1 when compared to spot density in the upper and lower regions of surface 1. In some embodiments, the reflective layer 7P is substantially flat about the z axis. In some embodiments, the reflective layer 7N is curved about the z axis. In some embodiments, the curvature of reflective layer 7N about z axis results in a convex shaped reflective layer, with the reflective side facing towards surface 1. An increased spot density in the central region may be desirable to compensate for effects such as losses in reflection or losses due to non-uniform aperture of reflective layers. In cases where such losses do not exist, both reflective layers may be designed to be substantially flat about the z axis to generate a uniform spot density in upper, central, and lower regions of surface 1. Upon illumination of surface 1, the beams, 8C and 8E, exit through reflective layer 7P. After exiting, beam 8E is incident on mirror 7O, focusing optical element 18E, neutral density filter 17E, and detected by image sensor 16H. Similarly, after exiting, beam 8C is incident on focusing optical element 18B, neutral density filter 17B, and detected by image sensor 16C. Images are captured from image sensors, 16D, 16I, 16H, 16C, are processed to find beam positions by computing the peak, centroid, or a similar parameter indicating beam spot position. This position data may be used to align reflective layers, 7P and 7N, surface 1, beam 2A, and mirror 7Y to achieve a uniform illumination intensity profile on surface 1.

Figure 3H:
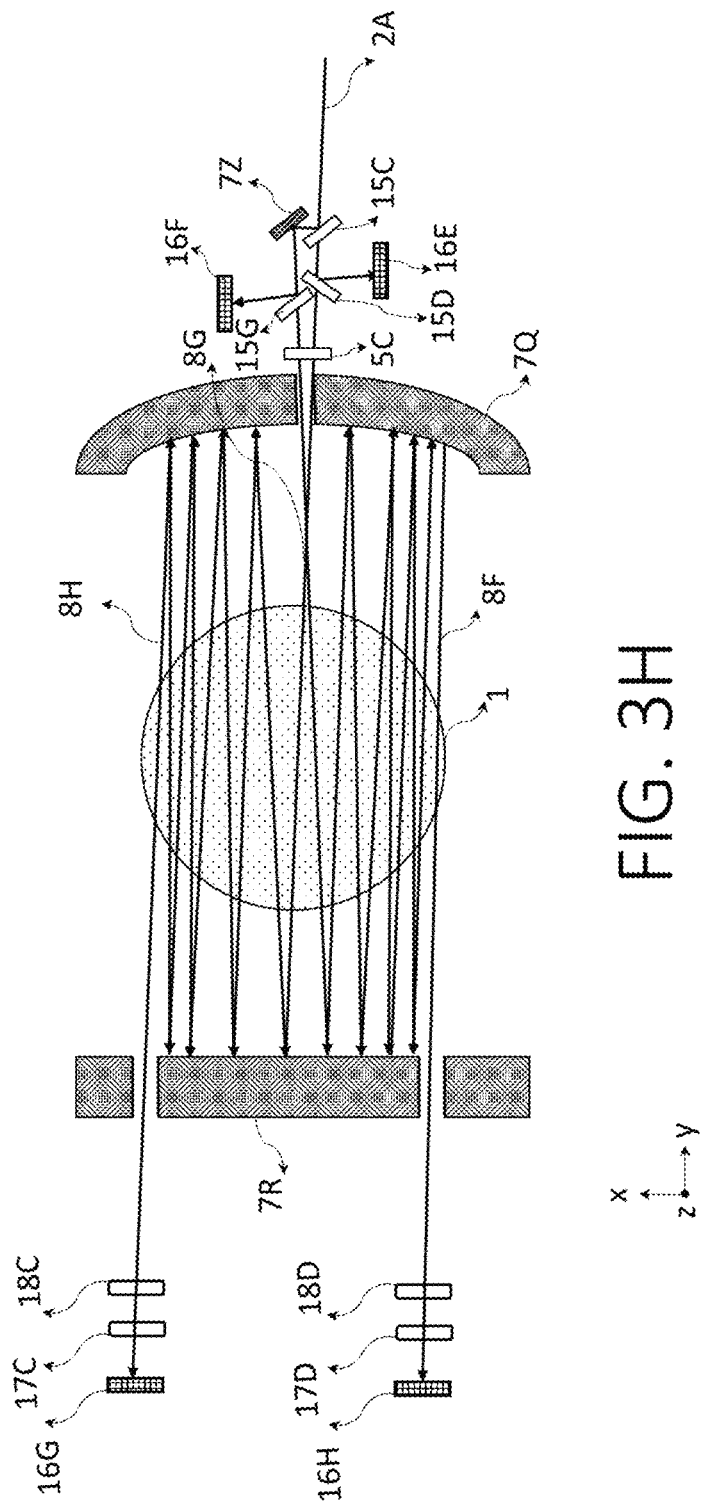
FIG. 3H illustrates reflective layers designed to increase number of reflections in upper and lower regions of a surface, in accordance with the invention.

FIG. 3H illustrates reflective layers, 7Q and 7R, designed to increase number of reflections in upper and lower regions of surface 1, according to some embodiments of the invention. An electromagnetic beam 2A is incident on a beam splitter 15C to generate transmitted and reflected beams. The transmitted beam from beam splitter 15C is incident on another beam splitter 15D. The reflected beam from beam splitter 15C is incident on a mirror 7Z and is incident on another beam splitter 15G. The beam splitters 15D and 15G generate transmitted and reflected beams. While the reflected beam from beam splitter 15D is detected by image sensor 16E, the reflected beam from beam splitter 15G is detected by image sensor 16F. The transmitted beams from beam splitter 15D is incident on beam expander 5C to generate expanded beam 8H, and the transmitted beam from beam splitter 15G is incident on beam expander 5C to generate expanded beam 8F. The expanded beams, 8H and 8F, are incident on reflective layer 7R. The expanded beams, 8H and 8F, undergo a plurality of reflections between reflective layers, 7R and 7Q, to illuminate surface 1. In some embodiments, beam 8H illuminates a region of surface 1 that is different from the region of surface 1 illuminated by beam 8F. The reflective layers, 7R and 7Q, are designed to generate an increased spot density in the upper and lower regions of surface 1 when compared to spot density in the central region of surface 1. In some embodiments, the reflective layer 7R is substantially flat about the z axis. In some embodiments, the reflective layer 7Q is curved about the z axis. In some embodiments, the curvature of reflective layer 7Q about z axis results in a concave shaped reflective layer, with the reflective side facing towards surface 1. An increased spot density in upper and lower regions of surface 1 may be desirable to compensate for effects such as losses in reflection or losses due to non-uniform aperture of reflective layers. In cases where such losses do not exist, both reflective layers may be designed to be substantially flat about the z axis to generate a uniform spot density in upper, central, and lower regions of surface 1. Upon illumination of surface 1, the beams, 8H and 8F, exit through reflective layer 7R. After exiting, beam 8H is incident on focusing optical element 18C, neutral density filter 17C, and detected by image sensor 16G. Similarly, after exiting, beam 8F is incident on focusing optical element 18D, neutral density filter 17D, and detected by image sensor 16H. Images are captured from image sensors, 16E, 16F, 16G, 16H, and processed to find beam positions by computing the peak, centroid, or a similar parameter indicating beam spot position. This position data may be used to align reflective layers, 7R and 7Q, surface 1, beam 2A, and mirror 7Z to achieve a uniform illumination intensity profile on surface 1.

Figure 3I:
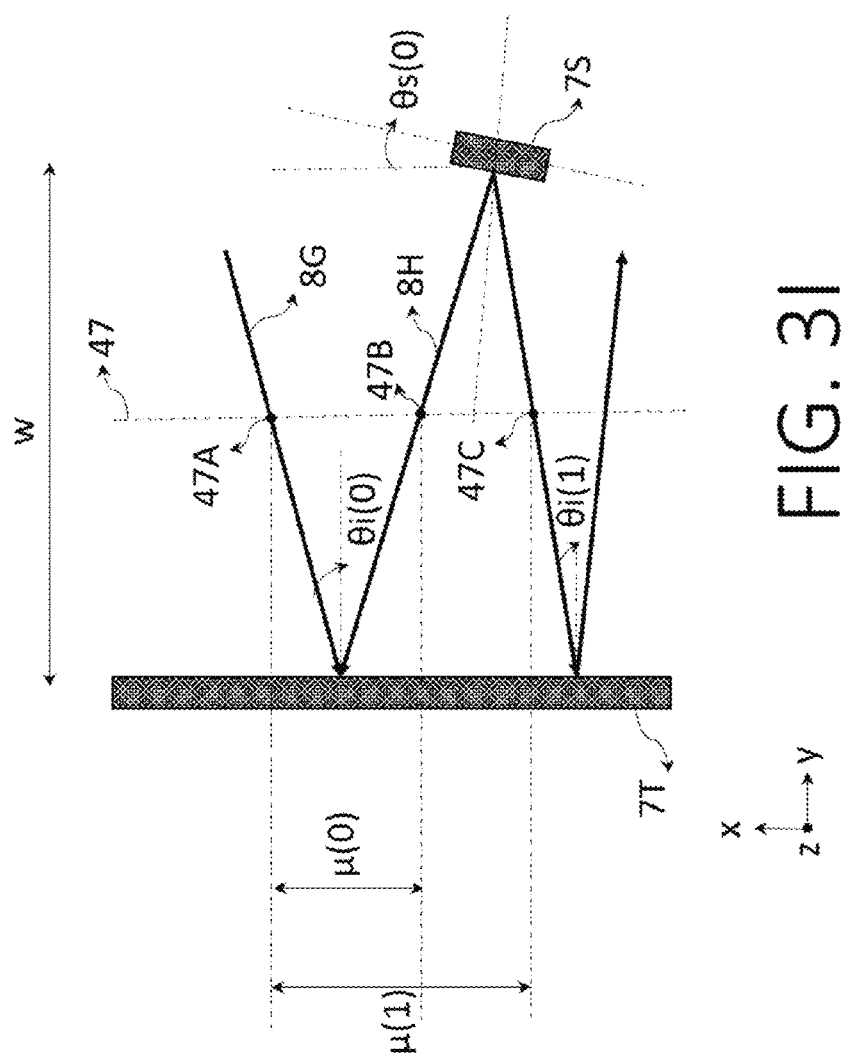
FIG. 3I depicts a method to design the curvature of a reflective layer, in accordance with the invention.

FIG. 3I depicts a method to design the curvature of reflective layers, 7S and 7T, according to some embodiments of the invention. A beam 8G is incident on a substantially flat reflective layer 7T at an angle $\theta_i(0)$ to illuminate a spot centered on point 47A. The reflected beam 8H from reflective layer 7T then illuminates a spot centered on point 47B and is incident on reflective layer 7S. The curvature of reflective layer 7S at the point of incidence of beam 8H is represented by angle $\theta_s(0)$. Upon reflection from reflective layer 7S, beam 8H illuminates a spot centered around point 47C and is incident on reflective layer 7T at an angle $\theta_i(1)$. $\mu(0)$ is the distance of point 47B from 47A, and $\mu(1)$ is the distance of point 47C from 47A. The position of point 47C along line 47 is dependent on $\theta_s(0)$. The angle $\theta_s$ can be used to adjust spot density. For example, a uniform spot density is generated (points 47A, 47B, and 47C are equally spaced) if $\theta_s(0)$ is zero. As $\theta_s(0)$ is increased, the distance between 47C and 47B becomes smaller. In other words, spot density increases as $\theta_s(0)$ is increased. Similarly, as $\theta_s(0)$ is decreased, the distance between 47C and 47B becomes larger. In other words, spot density decreases as $\theta_s(0)$ is increased. The curvature of reflective layer 7S can be designed according to desired spot density. Spot density is represented by a mean spot function $\mu$, which quantifies the mean position of spots. Mean spot function $\mu$ may be calculated according to the illumination intensity profile desired on a surface. In some embodiments, a uniform illumination intensity profile $C(x)$ may be desired. If there are negligible losses in reflection and losses due to aperture of reflective layers, then a periodically spaced mean spot function $\mu$, with the distance of separation between successive spots along x axis equal to spot width along x axis, may be sufficient to generate a substantially uniform illumination intensity profile. In situations where non-negligible losses exist due to losses in reflection and losses due to aperture of reflective layers, aperiodic spacing between spots may be useful to generate a uniform illumination intensity profile. Mean spot function $\mu$ can be determined with an optimization algorithm that minimizes the norm $$\left\| C(x) - \sum_{m=1}^{M} L_r(m) L_a(m) S(x, \mu(m), \sigma) \right\|,$$

where m is spot count, M is maximum spot count, $L_r(m)$ is reflection loss, $L_a(m)$ is aperture loss, and $S(x, \mu(m), \sigma)$ is a function describing the shape of a spot along x axis having a width $\sigma$ and located around mean location $\mu(m)$. In some embodiments, $L_r(m) = \alpha^{2m}$, where $\alpha$ is the reflection coefficient of surface. In some embodiments, $$S(x, \mu(m), \sigma) = e^{-(x-\mu(m))^2/2\sigma^2}.$$

In some embodiments, $S(x, \mu(m), \sigma)$ is a rectangular function $$\prod\left(\frac{(x-\mu(m))}{\sigma}\right).$$

Once mean spot function $\mu$ is computed, the curvature angle $\theta_s(m)$ of reflective layer 7S can be computed for different values of m from the equality, $$\frac{\sin(2(\theta_i(m) - \theta_s(m)))}{\cos(\theta_i(m) - 2\theta_s(m))} = \frac{2d\mu(m)\cos(\theta_i(m))}{l},$$

where $d\mu(m)$ is the first derivative of mean spot function $\mu(m)$, l is the distance between reflective layer 7T and reflective layer 7S, $$\theta_i(m=0) = \tan^{-1}\left(\frac{\mu(0)}{l}\right),$$

and $\theta_i(m+1) = \theta_i(m) - \theta_s(m)$. When $\theta_i(m)$ is small, small angle approximation may be used to express $\theta_s(m)$ and $\theta_i(m+1)$ in closed form as, $$\theta_s(m) = \theta_i(m) - \frac{d\mu(m)\cos(\theta_i(m))}{l}$$

and $$\theta_i(m+1) = \frac{d\mu(m)\cos(\theta_i(m))}{l}.$$

Figure 3J:
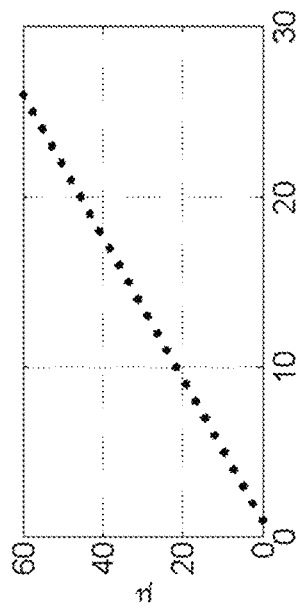
FIG. 3J shows a plot of intensity of illumination with respect to distance on surface, in accordance with the invention.

FIG. 3J shows a plot of intensity of illumination with respect to distance on surface, according to some embodiments of the invention. In this plot, the mean spot function $\mu(m)$ included spots periodically spaced with a period equal to $2.4\sigma$. The reflection loss is modeled as $L_r(m) = \alpha^{2m}$, where $\alpha^2 = 0.93$. The aperture loss is modeled as, $L_a(m) = 1$. The spot is modeled as a Gaussian, $$S(x, \mu(m), \sigma) = e^{-(x-\mu(m))^2/2\sigma^2}.$$

The illumination intensity is seen to decrease with increasing x coordinate due to cumulative reflection losses.

Figure 3K:
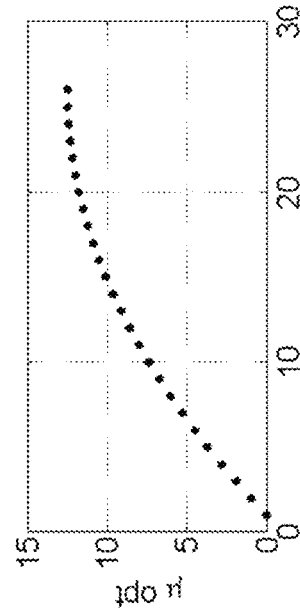
FIG. 3K shows a plot of the position of spots on inspection surface, in accordance with the invention.

FIG. 3K shows a plot of the position of spots on inspection surface, according to some embodiments of the invention. The spot position corresponds to the illumination intensity profile shows in FIG. 3J. The horizontal axis of the plot in FIG. 3K refers to spot count and the vertical axis refers to the mean spot position. The mean spot position is seen to be periodically increasing as the spot count increases.

Figure 3L:
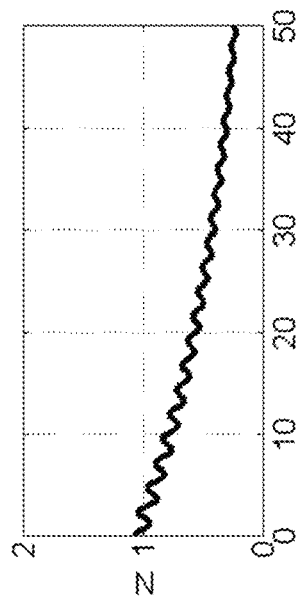
FIG. 3L shows a plot of optimized intensity of illumination with respect to distance on surface, in accordance with the invention.

FIG. 3L shows a plot of optimized intensity of illumination with respect to distance on surface, according to some embodiments of the invention. In order to compensate for the non-uniformity of illumination created by losses, an aperiodic mean spot function is used to increase spot density for higher values of x (i.e. for higher spot count values). $L_r(m)$, $L_a(m)$, and $S(x, \mu(m), \sigma)$ are same in FIG. 3L as they are in FIG. 3J. The effect of aperiodic mean spot function is the creation of a uniform illumination intensity profile within a predetermined region of x axis.

Figure 3M:
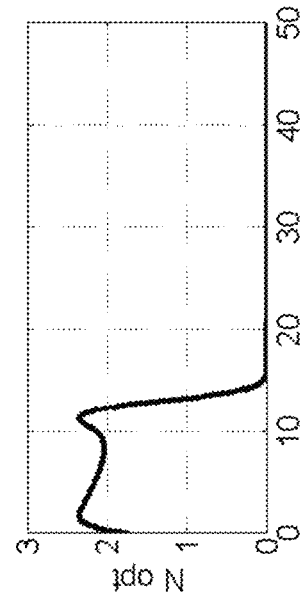
FIG. 3M shows a plot of the optimized position of spots on inspection surface, in accordance with the invention.

FIG. 3M shows a plot of the optimized position of spots on inspection surface, according to some embodiments of the invention. The spot position corresponds to the illumination intensity profile shown in FIG. 3L. The distance between spots is designed to be smaller at higher spot counts than they were at lower spot counts.

FIG. 3N shows a plot of the curvature of a reflective layer with respect to spot count, according to some embodiments of the invention. The horizontal axis refers to the spot count and the vertical axis refers to $\theta_s(m)$, the angle of a reflective layer. FIG. 3N is seen to be flat at zero degrees, resulting in a reflecting layer with zero curvature that creates a uniform spot density and non-uniform illumination density. $\theta_s(m)$ is calculated from the $\mu(m)$ data shown in FIG. 3K.

FIG. 3P shows a plot of the curvature $\theta_s(m)$ of a reflective layer with respect to spot position $\mu(m)$, according to some embodiments of the invention. FIG. 3P is seen to be flat at zero degrees, resulting in a reflecting layer with zero curvature that creates a uniform spot density. Such a uniform spot density may result in a non-uniform illumination density in the presence of reflection or aperture losses. $\theta_s(m)$ is calculated from the $\mu(m)$ data shown in FIG. 3K.

FIG. 3Q shows a plot of the optimized curvature $\theta_s(m)$ of a reflective layer with respect to spot count, according to some embodiments of the invention. $\theta_s(m)$ is calculated from the $\mu(m)$ data shown in FIG. 3M. In FIG. 3Q, $\theta_s(m)$ is seen to be increasing with respect to spot count, resulting in a curved reflecting layer that creates a non-uniform spot density. Such a non-uniform spot density may result in a uniform illumination density in the presence of reflection or aperture losses.

FIG. 3R shows a plot of optimized curvature $\theta_s(m)$ of a reflective layer with respect to spot position, according to some embodiments of the invention. $\theta_s(m)$ is calculated from the $\mu(m)$ data shown in FIG. 3M. In FIG. 3R, $\theta_s(m)$ is seen to be increasing with respect to mean spot position, resulting in a curved reflection layer that creates a non-uniform spot density. Such a non-uniform spot density may result in a uniform illumination density in the presence of reflection and aperture losses.

FIG. 4A illustrates a y-z cross-section showing the entry of a beam 8 through a reflective layer 7C located on the right, followed by reflection on a surface 1, and incidence on another reflective layer 7D located on the left, according to some embodiments of the invention. A beam 2B is incident on a beam expander 5 to generate an expanded beam 8. The expanded beam illuminates a spot on surface 1, and is incident on a reflective layer 7D. A defect present within the spot generates scattered light 4.

FIG. 4B illustrates a y-z cross-section showing the reflection of a beam 8 at a reflective layer 7D located on the left, followed by reflection on a surface 1, and incidence on another reflective layer 7C located on the right, according to some embodiments of the invention. Beam 8 illuminates a spot on surface 1. A defect present within the spot generates scattered light 4.

FIG. 4C illustrates a y-z cross-section showing the reflection of a beam 8 at a reflective layer 7C located on the right, followed by reflection on a surface 1, and incidence on another reflective layer 7D located on the left, according to some embodiments of the invention. Beam 8 illuminates a spot on surface 1. A defect present within the spot generates scattered light 4.

FIG. 4D illustrates a y-z cross-section showing the reflection of a beam 8 at a reflective layer 7C located on the right, followed by reflection on a wafer surface 1, and exit through another reflective layer 7D located on the left, according to some embodiments of the invention. Beam 8 illuminates a spot on surface 1.

Figure 5:
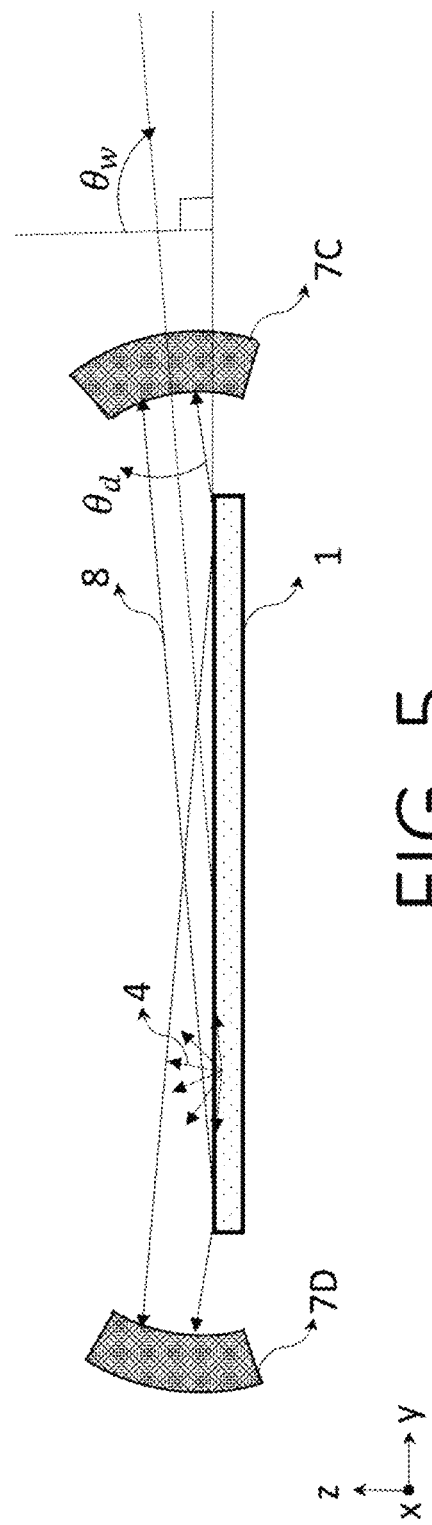
FIG. 5 illustrates a cross-section showing incidence angle and divergence angle of a beam, in accordance with the invention.

FIG. 5 illustrates a y-z cross-section showing incidence angle $\theta_w$ and divergence angle $\theta_d$ of a beam 8, according to some embodiments of the invention. The beam 8 undergoes a plurality of reflections on reflective layers 7C and 7D to illuminate surface 1. A defect on surface 1 generates scattered light 4. The reflection coefficient of surface 1 increases as $\theta_w$ increases. Large values of $\theta_w$ are desirable for reducing reflection losses. The beam 8 can be designed to be incident at an angle that maximizes reflected power from surface 1. The divergence angle $\theta_d$ of beam 8 is inversely proportional to beam width. The divergence angle $\theta_d$ is inversely proportional to the square root of Raleigh range. Rayleigh range of beam is proportional to square of beam width. Rayleigh range can therefore be increased significantly by increasing beam width. The dependence of Rayleigh range on beam width is used, together with information on incidence angle and dimensions of surface, to design reflective layers and beam expanders. Spot size on surface may be calculated from beam width and incidence angle of beam as, spot size=beam width/$\cos(\theta w)$. Spot size on wafer can be increased by increasing beam width and by increasing incidence angle $\theta_w$. The index of refraction of surface 1 exhibits a dependence on wavelength. The reflection coefficient of surface 1 increases as index of refraction increases. The beam 8 can be designed to have a wavelength that maximizes index of refraction and reflected power from surface 1. The reflection coefficient of a surface exhibits a dependence on polarization of beam 8. The beam 8 can be designed to have a polarization that maximizes reflected power from surface 1. In some embodiments, beam 8 is designed to be s polarized (polarized perpendicular to the plane of incidence) to the maximize reflection coefficient of surface.

Figure 6:
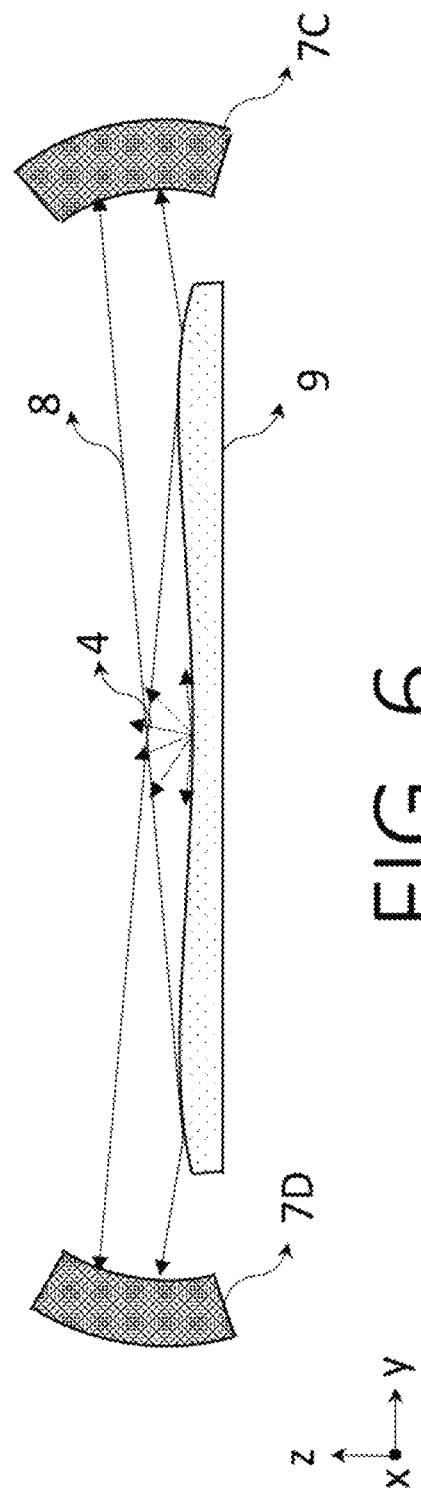
FIG. 6 illustrates a cross-section showing a beam illuminating a non-flat surface, in accordance with the invention.

FIG. 6 illustrates a y-z cross-section showing a beam 8 illuminating a non-flat surface 9, according to some embodiments of the invention. The beam 8 undergoes a plurality of reflections on reflective layers 7C and 7D to illuminate surface 1. A defect on surface 1 generates scattered light 4. In some embodiments, surface 1 may not be flat due to reasons including gravitational sag, non-uniform coatings, stress induced by coatings, and non-uniform polishing. Because of simultaneous illumination from both reflective layers, 7C and 7D, at a non-grazing angle, both peak and valley regions of wafer are illuminated. The angle of incidence $\theta_w$ of beam may be decreased to eliminate any shadows on wafer created by peak regions of wafer that prevent light from falling on valley regions. A key parameter of interest is the slope of flatness profile of surface 1. In some embodiments, the angle of incidence $\theta_w$ of beam is designed by taking the slope of flatness profile into consideration. In some embodiments, angle of incidence $\theta_w$ of beam is designed such that $(90-\theta_w)$ is larger than the maximum slope of flatness profile of surface 1.

FIG. 7A illustrates a y-z cross-section showing the entry of a beam 8 through a flat reflective layer 7E located on the right, followed by illumination of a flat surface 10 at grazing angle, and incidence on another flat reflective layer 7F located on the left, according to some embodiments of the invention. A defect present on surface 10 generates scattered light 4. Grazing angle refers to an angle of incidence $\theta_w$ that is close to 90 degrees. In other words, at a grazing angle, beam 8 is substantially parallel to surface 1

FIG. 7B illustrates a y-z cross-section showing the reflection of a beam 8 at a flat reflective layer 7F located on the left, followed by illumination of a flat surface 10 at grazing angle, and incidence on another flat reflective layer 7E located on the right, according to some embodiments of the invention.

FIG. 7C illustrates a y-z cross-section showing the reflection of a beam 8 at a flat reflective layer 7E located on the right, followed by illumination of a flat surface 10 at grazing angle, and incidence on another flat reflective layer 7F located on the left, according to some embodiments of the invention.

FIG. 7D illustrates a y-z cross-section showing the reflection of a beam at a flat reflective layer 7E located on the right, followed by illumination of a flat surface 10 at grazing angle, and exit through another flat reflective layer 7F located on the left, according to some embodiments of the invention. A defect present on surface 10 generates scattered light 4.

FIG. 8A depicts a y-z cross-section showing the illumination of a curved surface 1, according to some embodiments of the invention. A beam 8 undergoes a plurality of reflections between reflective layers, 7C and 7D, to illuminate the curved surface 1. The surface 1 is placed on a chuck 11A, which holds surface 1 at its edges in order to keep surface 1 in place. A defect on surface generates scattered light 4. Surface 1 is seen to exhibit a sag because of gravity. The curvature of surface 1 makes surface 1 behave like a concave mirror when beam 8 is incident on it. The exact curvature of surface 1 may be calculated from the properties of surface 1, including dimensions and material composition. The curvature thus calculated may be taken into account for the design of curvatures of reflective layers, 7C and 7D. In some embodiments, curvatures of reflective layers, 7C and 7D, are reduced to achieve an increased focal length to compensate for the curvature of surface 1.

FIG. 8B depicts a y-z cross-section showing the use of gas vents, 12A, 12B, and 12B, for holding surface 1 flat, according to some embodiments of the invention. A beam 8 undergoes a plurality of reflections between reflective layers, 7C and 7D, to illuminate surface 1. The surface 1 is placed on a chuck 11B, which holds surface 1 at its edges in order to keep surface 1 in place. A defect on surface generates scattered light 4. Surface 1 is seen to exhibit a sag because of gravity when there is no flow of gas through the vents. Sag of surface 1 is compensated to form a flat surface 1 by flowing gas through vents. In some embodiments, the flow of gas is such that gas is blown on the back side of surface 1. In some embodiments, the flow of gas is such that gas is sucked from the back side of surface 1.

FIG. 8C depicts a y-z cross-section showing the use of supporting structures, 13A, 13B, and 13C, that makes contact with surface 1 to hold the surface flat, according to some embodiments of the invention. A beam 8 undergoes a plurality of reflections between reflective layers, 7C and 7D, to illuminate surface 1. The surface 1 is placed on a chuck 11C, which holds surface 1 at its edges in order to keep surface 1 in place. A defect on surface 1 generates scattered light 4. Surface 1 is seen to exhibit a sag because of gravity when the supporting structures do not hold the wafer flat. Sag of surface 1 is compensated to form a flat surface 1 by raising the supporting structures through the gap between chuck 11C and surface 1.

FIG. 8D depicts a y-z cross-section showing the illumination of a flat surface 1, according to some embodiments of the invention. A beam 8 undergoes a plurality of reflections between reflective layers, 7C and 7D, to illuminate surface 1. The surface 1 is placed on a vacuum chuck 11D, which holds surface 1 at numerous points on the backside of surface with vacuum suction in order to keep surface 1 in place. A defect on surface generates scattered light 4. Surface 1 does not exhibit a sag because of gravity because it held flat by vacuum chuck 11D.

Figure 9:
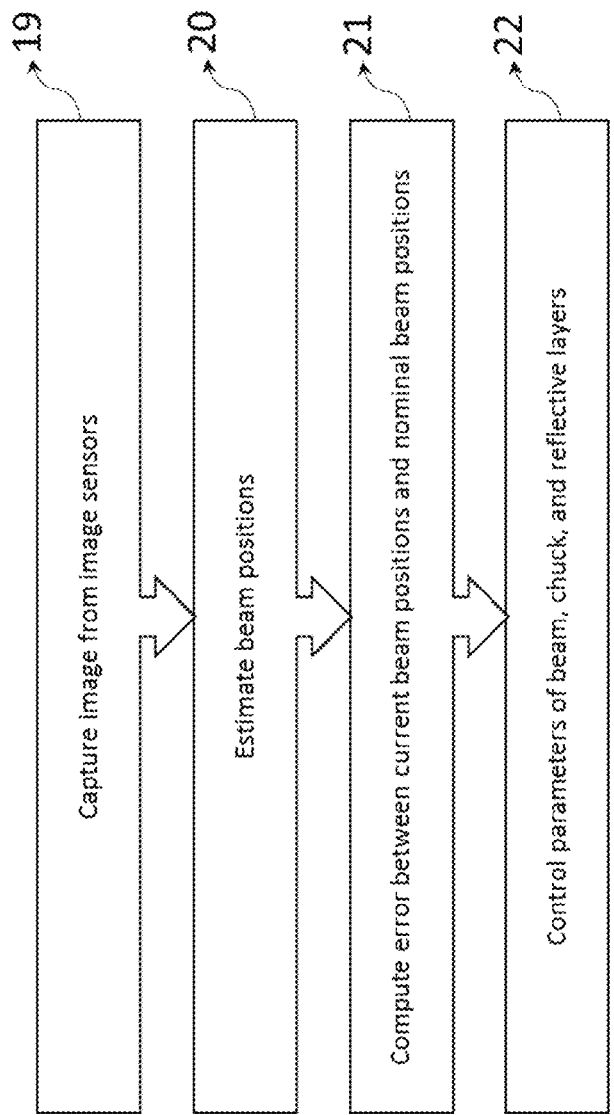
FIG. 9 shows a flow chart of a process to control beam position, in accordance with the invention.

FIG. 9 shows an exemplary flow chart of a process to control beam position, according to some embodiments of the invention. In block 19, images are captured from image sensors and are optionally stored in a memory. In block 20, the captured images are processed to estimate position information of beam. Position of a beam refers to horizontal and vertical coordinates of the center of beam on image sensor. In some embodiments, prior information about the shape of beam is used to estimate the position of beam accurately. For example, a model of beam shape with different position values can be iteratively fitted on captured data from image sensors. At each position value, least squares error value between model and captured data can be computed. The position value with the least error value can be determined as the estimate of the position of beam captured in images from image sensors. In some embodiments, centroid of beam can be used as an estimate for the position of beam. In some embodiments, peak of beam can be used as an estimate for the position of beam. In block 21, the estimated position of beam is compared with a nominal position of beam. Nominal position refers to ideal coordinates for beam position for achieving a predetermined incidence angle and a predetermined illumination intensity profile. Error values are computed by computing the difference of estimated and nominal beam positions. The flatness of surface can be evaluated by using this error information. In some embodiments, the surface is estimated as being flat when the error computed from measured and nominal positions of beam is zero. In some embodiments, a non-zero value of error corresponds to a deviation from a flat surface profile. In block 22, parameters of beam, chuck, and reflective layers are controlled to minimize error between estimated and nominal values of beam position. Beam parameters include three dimensional position, three dimensional orientation, and beam width. Chuck parameters include flow rate and direction of gas in gas vents and position of supporting structures. Reflective layer parameters include three dimensional position, three dimensional orientation, curvature, and mask aperture shape.

Figure 10:
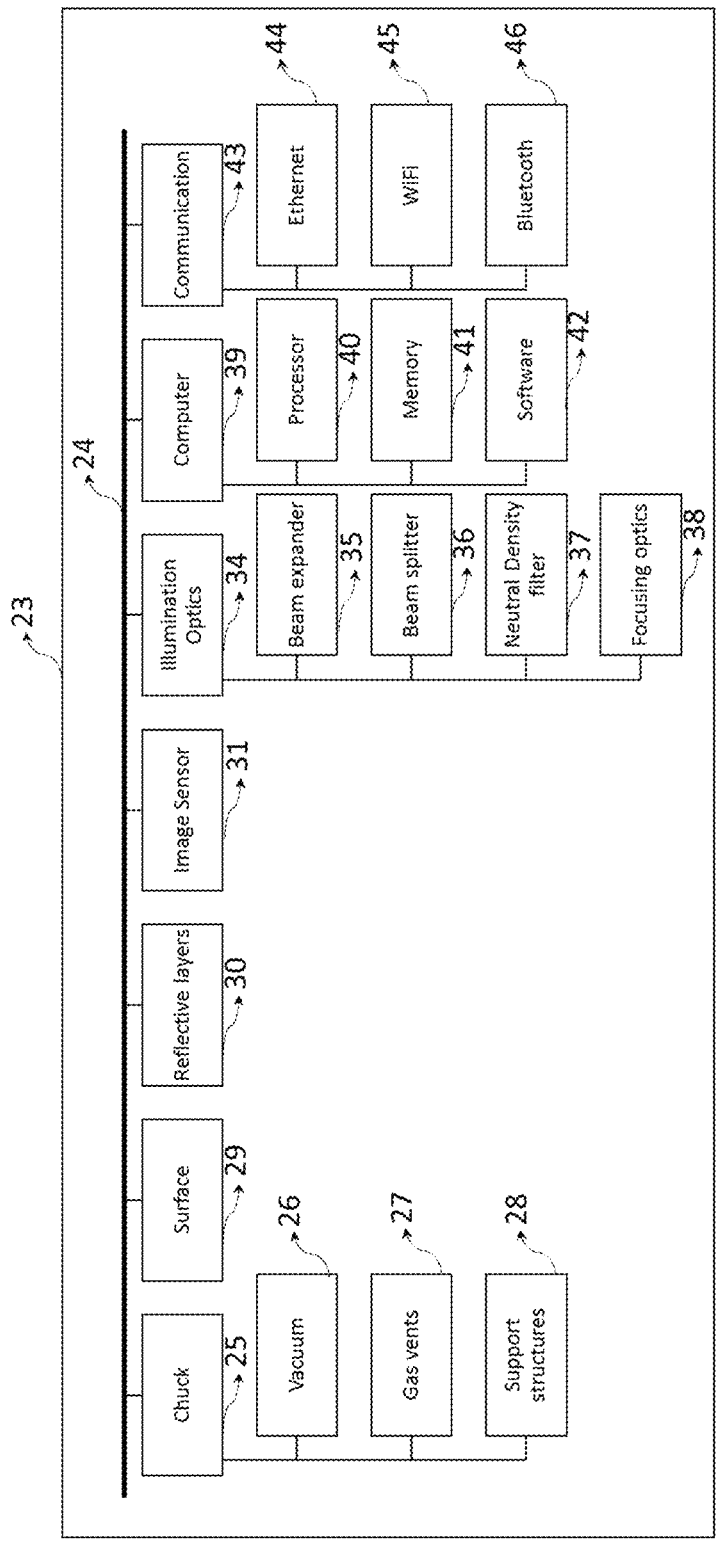
FIG. 10 depicts a block diagram of a wide field illumination system that can achieve a high illumination intensity, in accordance with the invention.

FIG. 10 depicts a block diagram 23 of a wide field illumination system that can achieve a high illumination intensity, according to some embodiments of the invention. A bus 24 connects various blocks such as chuck 25, surface 29, reflective layers 30, image sensor 31, illumination optics 34, computer 39, and communication 43. Data and control signals are carried by bus 24. Chuck 25 includes an edge handling system that holds the edge of surface 29, vacuum system 26 that holds the back side of surface 29 with vacuum suction, gas vents 27 and support structures 28 used to hold surface 29 flat. Surface 29 comprises the region to be illuminated by system 23. Surface 29 may be flat, curved due to gravity induced sag, or deformed due to coatings. Reflective layers 30 include reflection optics that illuminate surface 29 with a plurality of reflections. Image sensor 31 captures images of beams and transfers image data through bus 24 to computer 39. Image sensor 31 receives control information to adjust parameters such as exposure time and gain from computer through bus 24. Illumination optics 34 include mirror, beam expander 35, beam splitter 36, neutral density filter 37, and focusing optics 38. Computer 39 includes a processor 40, memory 41, and software 42. Software 42 processes image data from image sensor to compute information such as beam position. Software 42 generates control information and sends them through bus 24 to chuck 25, surface 29, reflection layers 30, image sensor 31, illumination optics 43. Computer 39 connects to communication block 43 for communicating data and control information through bus 24. Communication block 43 includes Ethernet 44, WiFi 45, and Bluetooth 46.

It will be recognized by those skilled in the art that various modifications may be made to the illustrated and other embodiments of the invention described above, without departing from the broad inventive scope thereof. It will be understood therefore that the invention is not limited to the particular embodiments or arrangements disclosed, but is rather intended to cover any changes, adaptations or modifications which are within the scope and spirit of the invention as defined by the appended claims.

It should be understood that the present invention as described above can be implemented in the form of control logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described above, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

The above description is illustrative and is not restrictive. Many variations of the disclosure will become apparent to those skilled in the art upon review of the disclosure. The scope of the disclosure should, therefore, be determined not with reference to the above description, but instead should be determined with reference to the pending claims along with their full scope or equivalents.

One or more features from any embodiment may be combined with one or more features of any other embodiment without departing from the scope of the disclosure. Further, modifications, additions, or omissions may be made to any embodiment without departing from the scope of the disclosure. The components of any embodiment may be integrated or separated according to particular needs without departing from the scope of the disclosure.

What is claimed is:

1. A system for illuminating a surface, comprising:
   a reflective layer around said surface;
   an electromagnetic beam incident on said layer;
   means for aligning said layer, said beam, and said surface so that said beam undergoes a plurality of reflections on said layer for illuminating a predetermined region of said surface,
   whereby the size of said region is larger than the size of said beam, and the intensity of illumination on said region is higher than the value obtained by multiplying the intensity of said beam and the ratio of the size of said beam to the size of said region.

2. The system of claim 1, wherein said beam is expanded with a beam expander to form a spot whose aspect ratio is larger than unity.

3. The system of claim 1, wherein said reflective layer and said surface are located within Rayleigh range of said beam.

4. The system of claim 1, wherein said reflective layer comprises a planar mirror.

5. The system of claim 1, wherein said reflective layer and said surface are located outside Rayleigh range of said beam.

6. The system of claim 1, wherein said reflective layer comprises a cylindrical mirror.

7. The system of claim 1, wherein said reflective layer has a variation in aperture to generate a variation in spot size on said surface.

8. The system of claim 1, wherein said reflective layer comprises a mask to attenuate reflection from predetermined region of said layer.

9. The system of claim 1, wherein said reflective layer produces a uniform spot density on said surface.

10. The system of claim 1, wherein said reflective layer produces a non-uniform spot density on said surface.

11. The system of claim 1, wherein said beam has a wavelength that maximizes reflected power from said surface.

12. The system of claim 1, wherein said beam has a polarization that maximizes reflected power from said surface.

13. The system of claim 1, wherein said beam is incident at an angle that maximizes reflected power from said surface.

14. The system of claim 1, wherein said surface is held flat by using a gas vent or a supporting structure.

15. The system of claim 1, wherein said surface is a cylinder or a cuboid.

16. A method for illuminating a surface, comprising:
   providing a reflective layer around said surface;
   directing an electromagnetic beam to be incident on said layer;
   aligning said layer, said beam, and said surface so that said beam undergoes a plurality of reflections on said layer for illuminating a predetermined region of said surface,
   whereby the size of said region is larger than the size of said beam, and the intensity of illumination on said region is higher than the value obtained by multiplying the intensity of said beam and the ratio of the size of said beam to the size of said region.

17. The method of claim 16, wherein said surface is evaluated for flatness by detecting said beam using an image sensor.

18. The method of claim 16, wherein said aligning comprises: capturing image from an image sensor; estimating beam position; computing difference between estimated beam position and nominal beam position; and controlling parameters of said beam, chuck, and said reflective layers to minimize said difference.

19. The method of claim 16, wherein said reflective layer has an aperture designed to illuminate said beam with a spot size that matches the size of said surface.

20. The method of claim 16, wherein said reflective layer generates a uniform illumination on said predetermined region of said surface.

* * * * *